(12) United States Patent  
Jennings et al.

(10) Patent No.: US 8,968,236 B2  
(45) Date of Patent: Mar. 3, 2015

(54) INJECTION DEVICE

(75) Inventors: Douglas Ivan Jennings, Royston (GB); Charles Michael Dean, Austin, TX (US)

(73) Assignee: Cilag GmbH International, Landis & Gyrstrasse (CH)

( * ) Notice: Subject to any disclaimer, the term of this patent is extended or adjusted under 35 U.S.C. 154(b) by 2076 days.

(21) Appl. No.: 11/910,539

(22) PCT Filed: Mar. 21, 2006

(86) PCT No.: PCT/GB2006/001030  
§ 371 (c)(1), (2), (4) Date: Mar. 10, 2011

(87) PCT Pub. No.: WO2006/106294  
PCT Pub. Date: Oct. 12, 2006

(65) Prior Publication Data  
US 2011/0245761 A1    Oct. 6, 2011

(30) Foreign Application Priority Data

Apr. 6, 2005 (GB) .................................. 0507002.4

(51) Int. Cl.  
*A61M 5/30* (2006.01)  
*A61M 5/20* (2006.01)

(52) U.S. Cl.  
CPC ....... *A61M 5/2033* (2013.01); *A61M 2005/206* (2013.01); *A61M 2005/208* (2013.01)  
USPC ........... 604/68; 128/204.25; 604/63; 604/134

(58) Field of Classification Search  
USPC .......... 128/204.25; 604/63, 68, 134, 257, 315  
See application file for complete search history.

(56) References Cited

U.S. PATENT DOCUMENTS 1,845,036 A    2/1932    Busher  
2,019,382 A    10/1935    Aronson  
(Continued)

FOREIGN PATENT DOCUMENTS

CH    518102 A    1/1972  
CN    2059579 U    7/1990  
(Continued)

OTHER PUBLICATIONS

European Search Report dated Aug. 3, 2011; Application No. 11170040.  
(Continued)

*Primary Examiner* — Nicholas Lucchesi  
*Assistant Examiner* — Gerald Landry, II

(57) ABSTRACT

An injection device (110) comprises a housing (112) adapted to receive a syringe (122) having a discharge nozzle (118), an actuator (114) and a drive (120) acted upon the syringe to advance it from a retracted position in which the discharge nozzle is contained within the housing to an extended position in which the discharge nozzle is contained within the housing to an extended position in which the discharge nozzle extends from the housing. There is a locking mechanism (HS) in communication with the actuator and activatable to be moved from a locked position in which the actuator is prevented from releasing the drive to an unlocked position in which the actuator is operable to act upon drive to advance the syringe. The locking mechanism or the housing includes integrally formed biasing means (210) adapted to return the locking mechanism to a locked position when it is not activated. There is no need for separate springs to be used bias to the releasable locking mechanism out the housing.

7 Claims, 3 Drawing Sheets

(56) References Cited

U.S. PATENT DOCUMENTS

| | | |
|---|---|---|
| 2,531,267 A | 11/1950 | Harisch |
| 2,764,977 A | 10/1956 | Ferguson |
| 2,828,742 A | 4/1958 | Ashkenaz |
| 3,131,692 A * | 5/1964 | Love ............................ 604/68 |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Ben Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A * | 3/1980 | Schmitz ..................... 604/138 |
| 4,222,380 A | 9/1980 | Terayama |
| 4,231,368 A | 11/1980 | Becker |
| 4,236,516 A | 12/1980 | Nilson |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,639,250 A | 1/1987 | Rycroft |
| 4,642,099 A * | 2/1987 | Phillips et al. ................ 604/136 |
| 4,676,530 A | 6/1987 | Nordgren et al. |
| 4,744,786 A | 5/1988 | Hooven |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A * | 4/1996 | McKinnon et al. ............. 604/72 |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A * | 2/1997 | Lilley et al. ..................... 604/68 |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A * | 2/1999 | Bachynsky ................... 604/134 |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A * | 12/1999 | Epstein et al. .................. 604/82 |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Adam et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Grecco |
| 6,258,068 B1 | 7/2001 | Kirchhofer et al. |

(56) References Cited

U.S. PATENT DOCUMENTS

| | | | |
|---|---|---|---|
| 6,270,479 B1 * | 8/2001 | Bergens et al. | 604/156 |
| 6,280,421 B1 | 8/2001 | Kirchhofer et al. | |
| 6,290,683 B1 | 9/2001 | Erez et al. | |
| 6,293,925 B1 | 9/2001 | Safabash et al. | |
| 6,317,939 B1 | 11/2001 | Malin | |
| 6,330,960 B1 | 12/2001 | Faughey et al. | |
| 6,332,875 B2 | 12/2001 | Inkpen et al. | |
| 6,371,939 B2 | 4/2002 | Bergens et al. | |
| 6,371,959 B1 | 4/2002 | Trice | |
| 6,387,078 B1 | 5/2002 | Gillespie, III | |
| 6,391,003 B1 | 5/2002 | Lesch, Jr. | |
| 6,419,658 B1 | 7/2002 | Restelli et al. | |
| 6,428,528 B2 | 8/2002 | Sadowski et al. | |
| 6,447,480 B1 | 9/2002 | Brunel | |
| 6,454,743 B1 | 9/2002 | Weber | |
| 6,454,746 B1 | 9/2002 | Bydlon et al. | |
| 6,461,333 B1 | 10/2002 | Frezza | |
| 6,491,667 B1 | 12/2002 | Keane et al. | |
| 6,517,517 B1 | 2/2003 | Farrugia et al. | |
| 6,537,252 B1 | 3/2003 | Hansen | |
| 6,544,234 B1 | 4/2003 | Gabriel | |
| 6,565,540 B1 | 5/2003 | Perouse et al. | |
| 6,565,553 B2 | 5/2003 | Sadowski et al. | |
| 6,569,115 B1 | 5/2003 | Barker et al. | |
| 6,569,123 B2 | 5/2003 | Aichas et al. | |
| 6,569,124 B1 | 5/2003 | Perouse | |
| 6,572,581 B1 | 6/2003 | Landua | |
| 6,575,939 B1 | 6/2003 | Brunel | |
| 6,585,702 B1 | 7/2003 | Brunel | |
| 6,589,210 B1 | 7/2003 | Rolfe | |
| 6,595,957 B1 | 7/2003 | Griffiths et al. | |
| 6,595,962 B1 | 7/2003 | Perthu | |
| 6,599,272 B1 * | 7/2003 | Hjertman et al. | 604/209 |
| 6,607,508 B2 | 8/2003 | Knauer | |
| 6,607,510 B2 | 8/2003 | Landau | |
| 6,613,022 B1 | 9/2003 | Doyle | |
| 6,620,137 B2 | 9/2003 | Kirchhofer et al. | |
| 6,638,256 B2 | 10/2003 | Jansen et al. | |
| 6,641,554 B2 | 11/2003 | Landau | |
| 6,641,560 B1 | 11/2003 | Bechtold et al. | |
| 6,641,565 B1 | 11/2003 | Lavi et al. | |
| 6,645,170 B2 | 11/2003 | Landua | |
| 6,645,181 B1 | 11/2003 | Lavi et al. | |
| 6,648,835 B1 | 11/2003 | Shemesh | |
| 6,648,850 B2 * | 11/2003 | Landau | 604/70 |
| 6,656,163 B1 | 12/2003 | Marshall et al. | |
| 6,673,049 B2 | 1/2004 | Hommann et al. | |
| 6,676,630 B2 | 1/2004 | Landau et al. | |
| 6,689,093 B2 | 2/2004 | Landau et al. | |
| 6,692,469 B1 | 2/2004 | Weekes et al. | |
| 6,699,220 B2 | 3/2004 | Rolfe | |
| 6,740,062 B2 | 5/2004 | Hjertman | |
| 6,743,199 B2 | 6/2004 | Shue et al. | |
| 6,743,203 B1 | 6/2004 | Pickhard et al. | |
| 6,746,429 B2 | 6/2004 | Sadowski et al. | |
| 6,767,336 B1 | 7/2004 | Kaplan | |
| 6,770,056 B2 | 8/2004 | Price et al. | |
| 6,776,777 B2 | 8/2004 | Barelle | |
| 6,783,509 B1 | 8/2004 | Landau et al. | |
| 6,793,161 B1 | 9/2004 | Fujia et al. | |
| 6,796,967 B2 | 9/2004 | Jensen | |
| 6,811,548 B2 | 11/2004 | Jeffrey | |
| 6,846,303 B2 | 1/2005 | Eakins et al. | |
| 6,875,205 B2 | 4/2005 | Leinsing | |
| 6,890,319 B1 | 5/2005 | Crocker | |
| 6,899,698 B2 | 5/2005 | Sams | |
| 6,932,793 B1 | 8/2005 | Marshall et al. | |
| 6,939,319 B1 | 9/2005 | Anstead et al. | |
| 6,979,316 B1 | 12/2005 | Rubin et al. | |
| 7,066,907 B2 | 6/2006 | Crossman et al. | |
| 7,097,071 B2 | 8/2006 | Anderson et al. | |
| 7,097,634 B2 | 8/2006 | Gilbert | |
| 7,118,553 B2 | 10/2006 | Scherer | |
| 7,156,823 B2 | 1/2007 | Landau et al. | |
| 7,160,913 B2 | 1/2007 | Schneider | |
| 7,294,122 B2 | 11/2007 | Kubo et al. | |
| 7,354,427 B2 | 4/2008 | Fangrow | |
| RE40,428 E | 7/2008 | Keane et al. | |
| 7,442,185 B2 | 10/2008 | Amark et al. | |
| 7,470,258 B2 | 12/2008 | Barker et al. | |
| 7,507,227 B2 | 3/2009 | Fangrow | |
| 7,510,547 B2 | 3/2009 | Fangrow | |
| 7,510,548 B2 | 3/2009 | Fangrow | |
| 7,513,895 B2 | 4/2009 | Fangrow | |
| 7,534,238 B2 | 5/2009 | Fangrow | |
| 7,547,300 B2 | 6/2009 | Fangrow | |
| 7,569,043 B2 | 8/2009 | Fangrow | |
| 7,618,396 B2 | 11/2009 | Slate et al. | |
| 7,635,356 B2 | 12/2009 | Stamp | |
| 7,645,271 B2 | 1/2010 | Fangrow | |
| 7,654,995 B2 | 2/2010 | Warren et al. | |
| 7,658,733 B2 | 2/2010 | Fangrow | |
| 7,678,333 B2 | 3/2010 | Reynolds et al. | |
| 7,682,345 B2 * | 3/2010 | Savage | 604/228 |
| 7,717,879 B2 | 5/2010 | Mansouri | |
| 7,744,561 B2 | 6/2010 | Stamp | |
| 7,759,654 B2 | 7/2010 | Yan et al. | |
| 7,794,434 B2 | 9/2010 | Mounce et al. | |
| 7,799,009 B2 | 9/2010 | Niedospial, Jr. et al. | |
| 7,811,262 B2 | 10/2010 | Moberg et al. | |
| 7,828,764 B2 | 11/2010 | Moberg et al. | |
| 7,871,397 B2 | 1/2011 | Schraga | |
| 7,879,010 B2 * | 2/2011 | Hunn et al. | 604/164.12 |
| 7,883,499 B2 | 2/2011 | Fangrow | |
| 7,959,715 B2 | 6/2011 | Kavazov et al. | |
| 7,972,321 B2 | 7/2011 | Fangrow | |
| 7,976,499 B2 | 7/2011 | Grunhut et al. | |
| 8,100,154 B2 | 1/2012 | Reynolds et al. | |
| 8,177,768 B2 | 5/2012 | Leinsing | |
| 8,277,414 B2 | 10/2012 | Barrow-Williams et al. | |
| 8,313,463 B2 | 11/2012 | Barrow-Williams et al. | |
| 8,409,138 B2 | 4/2013 | James et al. | |
| 8,491,530 B2 | 7/2013 | Maritan | |
| 8,696,628 B2 | 4/2014 | Grunhut | |
| 2001/0005781 A1 | 6/2001 | Bergens et al. | |
| 2001/0021828 A1 | 9/2001 | Fischer et al. | |
| 2001/0037087 A1 | 11/2001 | Knauer | |
| 2001/0037089 A1 | 11/2001 | Domici, Jr. | |
| 2001/0049496 A1 | 12/2001 | Kirchhofer et al. | |
| 2001/0051789 A1 | 12/2001 | Parsons | |
| 2002/0032412 A1 * | 3/2002 | Riemelmoser | 604/197 |
| 2002/0072709 A1 | 6/2002 | Sadowski et al. | |
| 2002/0095120 A1 | 7/2002 | Larsen et al. | |
| 2002/0151839 A1 | 10/2002 | Landau | |
| 2002/0161334 A1 | 10/2002 | Castellano et al. | |
| 2002/0165500 A1 | 11/2002 | Bechtold et al. | |
| 2002/0173752 A1 | 11/2002 | Polzin | |
| 2002/0183690 A1 | 12/2002 | Arnisolle | |
| 2003/0036679 A1 | 2/2003 | Kortenbach et al. | |
| 2003/0036725 A1 | 2/2003 | Lavi et al. | |
| 2003/0050609 A1 | 3/2003 | Sams | |
| 2003/0060773 A1 | 3/2003 | Nguyen | |
| 2003/0065286 A1 | 4/2003 | Landau | |
| 2003/0078546 A1 | 4/2003 | Jensen | |
| 2003/0088207 A1 | 5/2003 | Rogatchev et al. | |
| 2003/0088216 A1 | 5/2003 | Py | |
| 2003/0093030 A1 | 5/2003 | Landau | |
| 2003/0093035 A1 | 5/2003 | Mohammed | |
| 2003/0093036 A1 | 5/2003 | Crossman et al. | |
| 2003/0105430 A1 * | 6/2003 | Lavi et al. | 604/136 |
| 2003/0109833 A1 | 6/2003 | Sahpe | |
| 2003/0120212 A1 | 6/2003 | Dedig et al. | |
| 2003/0120222 A1 | 6/2003 | Vaillancourt | |
| 2003/0121815 A1 | 7/2003 | Bergeron et al. | |
| 2003/0135157 A1 | 7/2003 | Saulenas et al. | |
| 2003/0181859 A1 | 9/2003 | Brunel | |
| 2003/0184973 A1 | 10/2003 | Nagata et al. | |
| 2003/0196928 A1 | 10/2003 | Parsons | |
| 2003/0199814 A1 | 10/2003 | Parsons et al. | |
| 2003/0208164 A1 | 11/2003 | Botich et al. | |
| 2003/0212362 A1 | 11/2003 | Roser | |
| 2003/0212370 A1 | 11/2003 | Barrelle | |
| 2003/0212380 A1 | 11/2003 | Barrelle | |
| 2003/0225368 A1 | 12/2003 | Landau et al. | |

(56) References Cited

U.S. PATENT DOCUMENTS

| | | |
|---|---|---|
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1* | 12/2005 | Landau et al. .................. 604/70 |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1* | 12/2005 | Messerli et al. .............. 604/240 |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1* | 8/2006 | Hommann et al. ........... 604/137 |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0071225 A1* | 3/2008 | Hommann et al. ........... 604/198 |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0245761 A1* | 10/2011 | Jennings et al. ................ 604/68 |
| 2011/0282215 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0096314 A2 | 5/1983 |
| EP | 0111724 B1 | 11/1983 |
| EP | 0144625 A2 | 6/1985 |
| EP | 0240787 A2 | 3/1987 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |

(56) References Cited

FOREIGN PATENT DOCUMENTS

| | | |
|---|---|---|
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| JP | 59-115053 A | 7/1984 |
| JP | 2-185261 A | 7/1990 |
| JP | 2-502971 T | 9/1990 |
| JP | H02-29960 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2008-284177 A | 11/2008 |
| NZ | 335985 A | 4/2001 |
| NZ | 573171 A | 11/2010 |
| NZ | 573350 A | 12/2010 |
| WO | WO 88/08725 | 11/1988 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | 02/074361 A1 | 9/2002 |
| WO | 03/015846 A2 | 2/2003 |
| WO | WO 03/013632 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |

(56) References Cited

FOREIGN PATENT DOCUMENTS

| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | 2004/101025 A2 | 11/2004 |
| WO | WO 2004/108194 A1 | 12/2004 |
| WO | 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | 2005/105014 A2 | 11/2005 |
| WO | 2005/115516 A1 | 12/2005 |
| WO | 2005/120607 A2 | 12/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/120607 A2 | 12/2005 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | 2007/129324 A2 | 11/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | 2010/023303 A1 | 3/2010 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.

(56) References Cited

OTHER PUBLICATIONS

Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11163779.9.
Singapore Search Report dated Mar. 15, 2012; Application No. Sg 201007017-5.
European Search Report dated Jul. 20, 2011; Application No. 11163762.5.
Australian Search Report dated Feb. 26, 2008; Application No. SG 2006080717.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
Australian Search Report dated Dec. 11, 2007; Application No. 200608165-7.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug., 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.

\* cited by examiner

US 8,968,236 B2

INJECTION DEVICE

CROSS REFERENCE TO RELATED APPLICATIONS

The present application is a 35 U.S.C. 371 National Stage Application of PCT/GB2006/001030 filed Mar. 21, 2006, which claims priority to European Patent Application No. 0507002.4 filed Apr. 6, 2005, the entire contents of which are incorporated entirely herein by reference.

FIELD OF THE INVENTION

The present invention relates to an injection device of the type that receives a syringe, extends it, discharges its contents and then retracts it automatically.

BACKGROUND OF THE INVENTION

Known injection devices are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

It is known to provide a safety interlock around the needle of such injection devices.

Such a safety interlock prevents accidental activation of a trigger of the injection device by preventing rotation of the trigger. The interlock is sprung loaded out of the aperture through which the syringe extends once activated. The interlock is disengaged by pressing it in towards the aperture by, for example, pressing it against a user's body, thereby allowing the trigger to be activated and the syringe to be extended.

The interlock has to be biased out of the aperture so that it can be activated. Known devices use small coil springs positioned between the housing of the injection device and the interlock. These small springs are costly to assemble and introduce a risk that they may be missed out all together during the manufacturing process.

SUMMARY OF THE INVENTION

The injection device of the present invention is designed to deal with the aforementioned problems.

In view of the foregoing, there is provided, in a first aspect of the present invention, an injection device comprising:
  a housing adapted to receive a syringe having a discharge nozzle;
  an actuator;
  a drive acted upon by the actuator and in turn acting on the syringe to advance it from a retracted position in which the discharge nozzle is contained within the housing to an extended position in which the discharge nozzle extends form the housing;
  a locking mechanism in communication with the actuator and activatable to be moved from a locked position in which the actuator is prevented from releasing the drive to an unlocked position in which the actuator is operable to act upon the drive to advance the syringe;
  characterised in that the locking mechanism or the housing includes integrally formed biasing means adapted to return the locking mechanism to a locked position when it is not activated.

Hence, there is no need to provide small springs to bias the locking mechanism into its locked position. This reduces the cost and complexity of assembly of the injection device.

In one embodiment of the present invention, the locking mechanism includes the integrally formed biasing means.

Preferably, the biasing means comprises at least one resilient arm integrally formed with the locking mechanism.

The locking mechanism can be arranged in the housing such that the resilient arm is biased against a surface of the housing on activation.

Generally, the locking mechanism is arranged in the housing such that it extends from the housing when it is in its unlocked position and slides into the housing on activation.

In one embodiment of the present invention, the internal surface of the housing comprises a cam against which the resilient arm is biased on activation such that the spring force in the resilient arm increases according to the distance by which the locking mechanism is slid into the housing from its unlocked position.

The cam provides a mechanical advantage so that the arms can be designed for a higher spring rate with shorter travel than that necessarily required to disengage the locking mechanism.

Preferably, the locking mechanism comprises a plurality of resilient arms, wherein the housing includes a corresponding cam surface on the internal surface of the housing against which each resilient arm is biased on activation. Most preferably, the locking mechanism comprises two arms.

BRIEF DESCRIPTION OF THE DRAWINGS

The invention will now be described by way of example with reference to the accompanying drawings, in which.

DETAILED DESCRIPTION OF THE DRAWINGS

Figure 1:
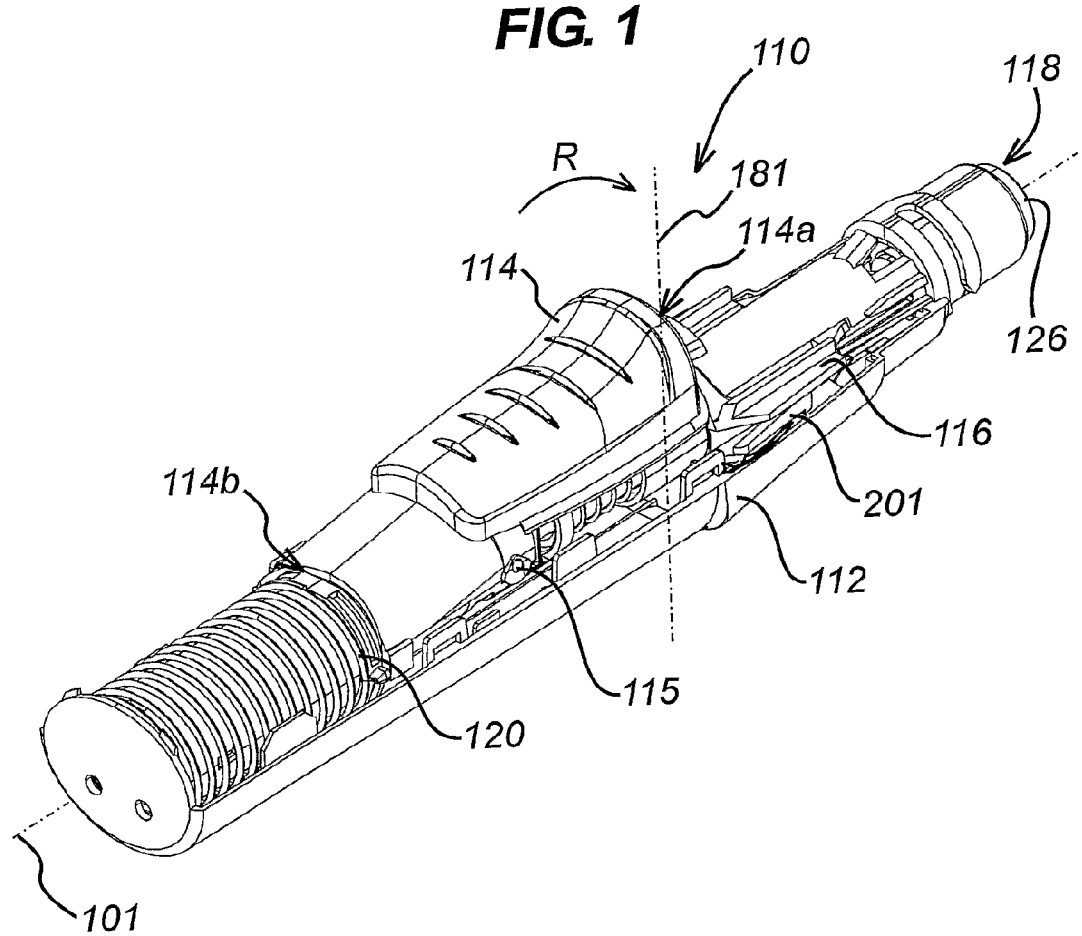
FIG. 1 shows a perspective view of an injection device according to the present invention without an upper section of its housing.
Figure 2:
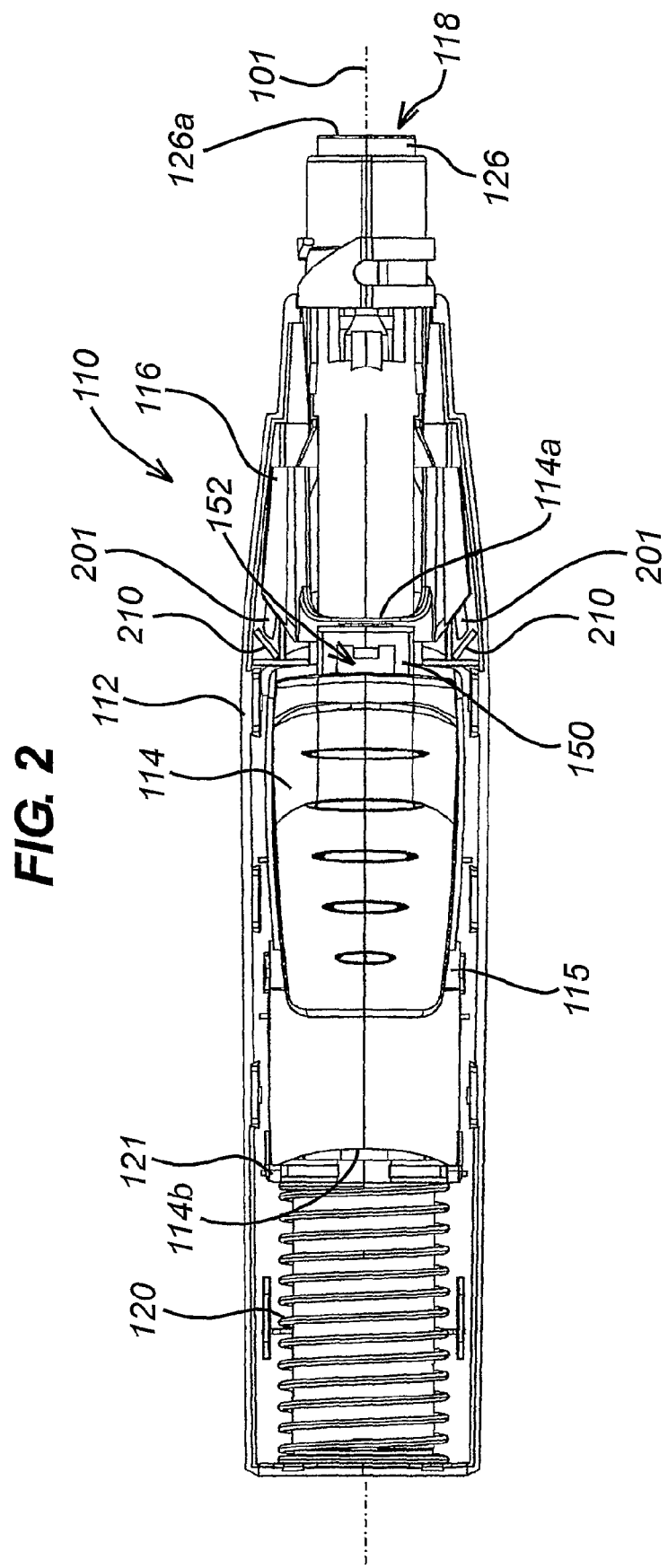
FIG. 2 shows a top-side view of the injection device shown in FIG. 1.

FIGS. 1 and 2 show an injection device 110 according to a first embodiment of the present invention. The injection device 110 has an injection device housing 112 and a longitudinal axis 101.

A syringe (not shown) is contained in the housing 112. The injection device 110 comprises trigger 114 (actuator) and a releasable locking mechanism 116. The trigger 114 has a first end 114a and a second end 114b. The trigger 114 is rotatable about a pivot 115 from a rest position (as shown in FIG. 2) to an active position. The second end 114b of the trigger 114 connects with a drive coupling 121 which is acted upon by a drive spring 120. The drive coupling 121 is in communication with the syringe 122.

Rotation of the trigger 114 about the pivot 115 in a direction R (i.e. downwards into the housing 112 at its first end 114a) causes the second end 114b of the trigger 114 to disengage from the drive coupling 121, thereby letting the drive spring 120 drive the syringe 122 (via the drive coupling 121) along the longitudinal axis 101 and out of an aperture 118 in the housing 112.

The releasable locking mechanism 116 is in communication with sliding sleeve 126 which protrudes, when in a first position, from the aperture 118 in the housing 112. The locking mechanism 116 is deactivated by movement of the sliding sleeve 126 along the longitudinal axis 101 into the housing 112 into a second position.

A first end 126a of the sliding sleeve 126 can be placed against a body into which drug is being delivered, thereby deactivating the releasable locking mechanism 116 and allowing the trigger 114 to rotate in direction R from its rest position to its active position.

The trigger 114 is provided at its first end 114a with a first portion 150 having a cut-out 152. The first portion 150 extends from the first end 114a of the trigger 114a in a direction substantially parallel to the longitudinal axis 101.

The releasable locking mechanism 116 includes a protrusion 154 which projects in a direction along a perpendicular axis 181 which is perpendicular to the longitudinal axis 101. The cut-out 152 is dimensioned to receive the protrusion.

When the releasable locking mechanism 116 is in its first position, an end of the protrusion abuts an under-surface of the first portion 150, thereby preventing rotation of the trigger 114.

When the releasable locking mechanism 116 is in its second position (not shown) following movement of the sliding sleeve 126 into the housing 112, the cut-out 152 is positioned above the end of the protrusion 154 allowing it to pass over the protrusion 154 when a downwards force is applied the trigger 112. Hence, the trigger 112 is no longer prevented from rotating and disengages itself from the drive coupling 121, thereby extending the syringe 122.

Figure 3:
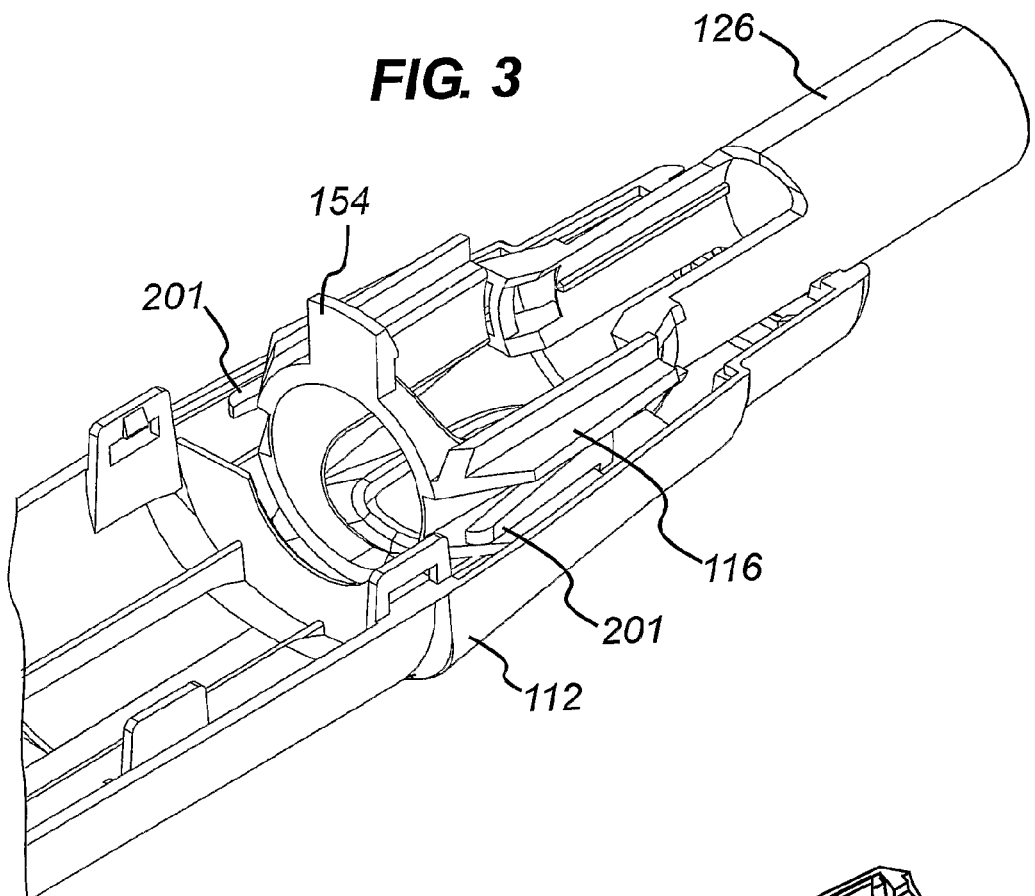
FIG. 3 shows an expanded perspective view of the housing and releasable locking mechanism of the injection device of the present invention.
Figure 4:
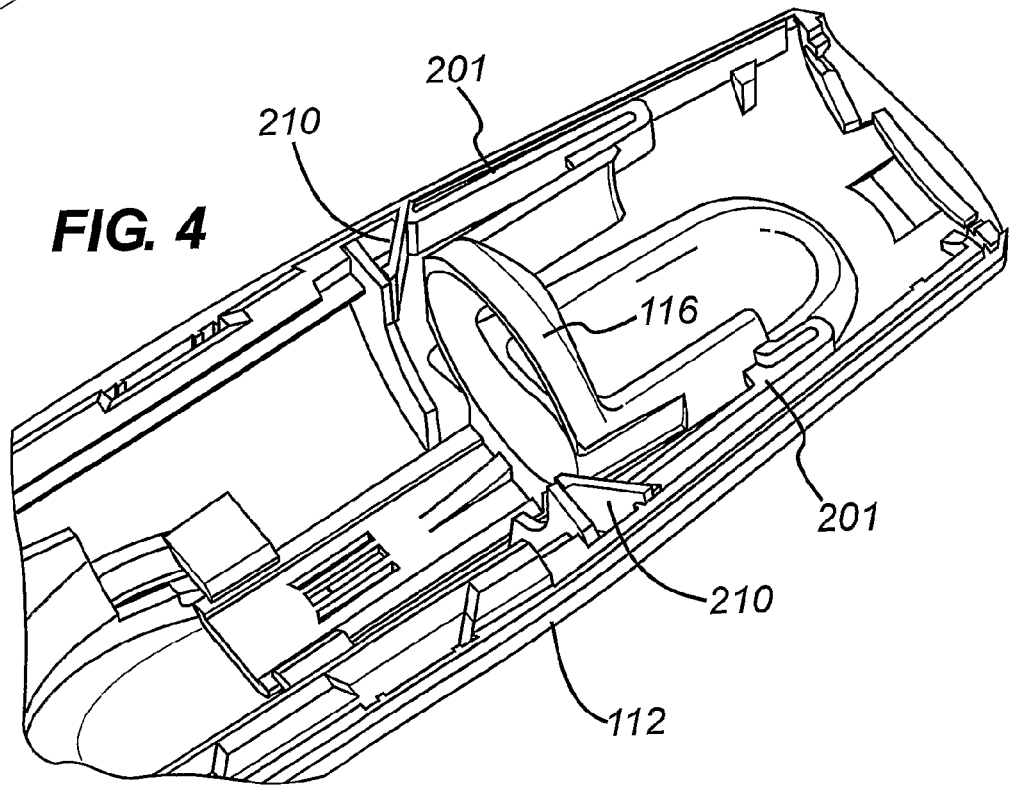
FIG. 4 shows an alternative expanded perspective view of the housing and releasable locking mechanism of the injection device of the present invention.

As can be seen in FIGS. 3 and 4, the releasable locking mechanism 116 is provided with a pair of integrally formed resilient arms 201. The resilient arms 201 flex resiliently in a direction away and towards the releasable locking mechanism 116.

The housing 112 comprises a pair of camming surfaces 210 which are positioned in line with the resilient arms 201 towards the end of the point in the housing 112 at which the locking mechanism 116 is disengaged.

The resilient arms 201 communicate with the camming surfaces 210 such that, as the sleeve 126 is pressed into the housing 112, the arms 201 bias the releasable locking mechanism 116 and sleeve 126 out of the opening 126. In this way, when no force is applied to the end 126a of the sleeve, the releasable locking mechanism 116 remains engaged preventing actuation of the trigger.

It will be appreciated that any configuration of integrally-formed resilient biasing may be used in place of the arms 201.

The present invention provides the significant advantage that the biasing of the releasable locking mechanism 116 is integral with the mechanism itself, thereby obviating the need for small springs which are complex and costly to assemble. Alternatively, the skilled person will appreciate that the resilient arms 201 could be mounted on the housing 112 and communicate with a surface of the releasable locking mechanism 116.

It will of course be understood that the present invention has been described above purely by way of example and modifications of detail can be made within the scope of the invention.

The invention claimed is:

1. An injection device comprising:
a housing adapted to receive a syringe having a discharge nozzle;
an actuator;
a drive acted upon by the actuator and in turn acting on the syringe to advance it from a retracted position in which the discharge nozzle is contained within the housing to an extended position in which the discharge nozzle extends from the housing through an aperture;
a locking mechanism in communication with the actuator and activatable to be moved from a locked position in which the actuator is prevented from releasing the drive to an unlocked position in which the actuator is operable to act upon the drive to advance the syringe;
characterized in that the locking mechanism or the housing includes integrally formed biasing means adapted to return the locking mechanism to a locked position when it is not activated, wherein the locking mechanism is in communication with a sliding sleeve which protrudes, when in a first position, from the aperture in the housing, wherein the locking mechanism is moved to its unlocked position by movement of the sliding sleeve into the housing and into a second position.

2. The injection device of claim 1, wherein the locking mechanism included the integrally formed biasing means.

3. The injection device of claim 2, wherein the biasing means comprises at least one resilient arm integrally formed with the locking mechanism.

4. The injection device of claim 3, wherein the locking mechanism is arranged in the housing such that the resilient arm is biased against a surface of the housing on activation.

5. The injection device of claim 4, wherein the locking mechanism is arranged in the housing such that it extends from the housing when it is in its unlocked position and slides into the housing on activation.

6. The injection device of claim 5, wherein the internal surface of the housing comprises a cam against which the resilient arm is biased on activation such that the spring force in the resilient arm increases according to the distance by which the locking mechanism is slid into the housing from its unlocked position.

7. The injection device of claim 6, wherein the locking mechanism comprises a plurality of resilient arms, wherein the housing includes a corresponding cam surface on the internal surface of the housing against which each resilient arm is biased on activation.

* * * * *